United States Patent
Cherkassky

(10) Patent No.: US 8,298,571 B2
(45) Date of Patent: Oct. 30, 2012

(54) PRODUCT AND METHOD FOR REDUCING SUBSTANCE CRAVING

(76) Inventor: Michael Cherkassky, Fort Worth, TX (US)

( * ) Notice: Subject to any disclaimer, the term of this patent is extended or adjusted under 35 U.S.C. 154(b) by 0 days.

(21) Appl. No.: 12/806,668

(22) Filed: Aug. 19, 2010

(65) Prior Publication Data

US 2010/0316692 A1    Dec. 16, 2010

Related U.S. Application Data

(63) Continuation-in-part of application No. 12/218,968, filed on Jul. 21, 2008, now abandoned.

(51) Int. Cl.
*A61K 47/00* (2006.01)
(52) U.S. Cl. ........................................................ 424/439
(58) Field of Classification Search .................. None
See application file for complete search history.

(56) References Cited

U.S. PATENT DOCUMENTS 3,928,252 A * 12/1975 Rigler et al. .................. 426/573
H2095 H * 1/2004 Young ........................... 426/658

FOREIGN PATENT DOCUMENTS

JP    60352857 A  *  3/1988

OTHER PUBLICATIONS

1966 Kraft Miracle Margarine Corn Oil Muffin print ad, accessed online Jan. 19, 2012.*

* cited by examiner

*Primary Examiner* — Anand Desai
*Assistant Examiner* — Melissa Mercier
(74) *Attorney, Agent, or Firm* — Lynn E. Barber

(57) ABSTRACT

A composition and method are provided that are effective for reduction or elimination of the craving foods and other substances for which a patient wishes to reduce consumption or intake. The composition is a paste made of a binder, and non-binder ingredients of mustard, pepper and salt, and optionally a sweetener. The composition of the invention is administered on the tongue as a paste.

8 Claims, No Drawings

PRODUCT AND METHOD FOR REDUCING SUBSTANCE CRAVING

CROSS-REFERENCE TO RELATED APPLICATIONS

This application is a continuation-in-part application of U.S. patent application Ser. No. 12/218,968 filed Jul. 21, 2008 now abandoned.

BACKGROUND OF THE INVENTION

1. Field of the Invention

This invention relates to preparations that reduce craving for food substances and craving for other substances that are orally consumed or otherwise orally provided, such as the smoking of tobacco. In particular the invention relates to preparations and a method for reducing oral craving and allows patients to eliminate or greatly reduce the dependence on substances which they crave.

2. Description of the Related Art

Overweight and obesity are major problems in the western community due to increased consumption and changes in nutritional value of foods that are consumed. Many humans, and their companion animals, suffer from overweight. Today obesity is one of the most serious health problems in the United States, with approximately 30% of adults suffering from obesity, and at least 50% of adults in the United States being overweight. The problem of obesity in the United States and most western countries has been steadily increasing in the last several decades. Such obesity has caused or contributed to a marked increase in the occurrence of heart diseases, hypertension, diabetes, arthritis and increased morbidity and mortality. There is also recent research which links obesity with different types of cancer, particularly breast cancer. Obesity is a serious public health hazard, second in importance only to tobacco. Being overweight reduces lifespan as well as quality of life.

There are many methods suggested for management of obesity and overweight. These include diets that exclude fats and high caloric elements, appetite suppressants, psychotherapeutic techniques and operative techniques. One of the most common methods is the use of stimulants. Amphetamine-like agents act on the brain to reduce the sensation of hunger. Experience indicates that most of the appetite suppressants work for a short period of time, but a few weeks or a few months later they lose most of their potency and patients start regaining weight. There is also a serious problem with the maintenance of a desirable weight after it is achieved, for the simple reason that appetite suppressants cannot be continued indefinitely at full strength.

The reason that most people become overweight is that they consume more nutrition calories than they require, often primarily because of cravings for certain foods, such as chocolate or potato chips. In other words, humans do not only eat to survive, but also eat for the taste, flavor and gratification. The degree of the satiety has changed and is predicated not only the necessary nutritional requirements but also on unphysiological "unnatural" pleasure drive.

The complex mechanism that is triggered in the mammalian body during food digestion is characterized by multiple interdependent processes where different hormones with multiple functions influence different organs at the same time, and by that means allow the whole body to function properly.

One of the necessary sensations which completes the mechanism of digestion is satiety. There are many unknown areas in our knowledge of satiety, but the number hormones known to participate in the process of digestion also play a significant role inducing a sense of satiety.

Gastrointestinal peptides are predominantly polypeptides produced in and secreted from specialized gut endocrine cells as well as nerves. The production of gastrointestinal hormones increases when gut endocrine cells are stimulated by food, intraluminal pH, releasing factors, other transmitters or hormones. A number of fairly well-known gastrointestinal hormones are amylin, CCK (cholecystokinin), gastrin, secretin, enterostatin, and neuropeptide Y [3-36]. All of these hormones play their specific role in digestion processes confined to the intestinal tract, and also participate in transmitting information to the brain enabling the brain to be well appraised of the quantity and quality of food being consumed and thus modulating and regulating the amount of food intake from meal to meal. Information from the gastrointestinal tract and oropharynx is newly transmitted to the brain.

It has been proven that hormones reach tractus solitarius via the hypothalamus and concentrating there, they induce satiety, among them CCK, amylin and possibly insulin. Amylin and CCK also reduce gastric emptying and intestinal mobility and thus delay the delivering of food to the intestines and contribute to the early sense of the satiety and as a result limit the overall quantity of food being consumed during a particular meal.

The hazards of tobacco smoking due to coal tars, carbon monoxide and nicotine are well-known. Most lung cancers are the result of tobacco smoking, as are cancers of the urinary bladder, and a variety of heart and circulation problems and high blood pressure. There are very many Americans who try to stop smoking each year, most of whom do not succeed. The difficulties inherent in ending the use of tobacco are great and are the result of the effect of nicotine withdrawal syndrome, which presents itself in increased tension, irritability, restlessness, intense craving, depression, bradicardia, hypotension, constipation, sleep disturbance and increased body weight. The invention herein alleviates the problems related to tobacco smoking by reducing or eliminating the craving for smoking.

It is therefore an object of the invention to provide a product and a treatment method using certain food ingredients in a manner that reduces or eliminates the craving for eating of foods for which the patient wishes to reduce consumption. Such ingredients preferably include but are not limited to margarine, mustard, pepper and salt.

It is a further method of the invention herein to provide a product and a treatment method that reduce the craving for tobacco.

Other objects and advantages will be more fully apparent from the following disclosure and appended claims.

SUMMARY OF THE INVENTION

The invention herein is a composition and method effective for reduction or elimination of the craving for eating of foods for which a patient wishes to reduce consumption, and alternatively, for tobacco. Such ingredients preferably include but are not limited to a binder such as margarine, mustard, pepper and salt, and optionally a sweetener. The composition of the invention is preferably applied to the surface of the tongue as a paste, and then the craved substance is administered orally with the paste or with the non-binder components of the paste.

Other objects and features of the inventions will be more fully apparent from the following disclosure and appended claims.

DETAILED DESCRIPTION OF THE INVENTION AND PREFERRED EMBODIMENTS THEREOF

The present invention in its preferred embodiment includes the administration to mammals, and in particular, humans, of a variety of specially combined food ingredients, mostly with limited nutritional value, which in combination are capable of reduction or elimination of the craving for eating of a substance (such as solid foods or liquids for which a patient wishes to reduce consumption), and alternatively, for a tobacco product (such as smoking of cigarettes). Such ingredients preferably include a binder, such as margarine, and non-binder components, including various seasonings, and preferably include but are not limited to margarine, mustard, pepper and salt. The composition of the invention is administered orally, preferably in the form of a paste as discussed herein.

The proportion of ingredients can vary, and additional ingredients may be included.

The composition of the invention is preferably prepared by mixing the ingredients to form a paste.

In addition, the product of the invention herein for reducing craving can be combined with currently commercially available or future preparations without detrimental effect because of the lack of side effects of the invention herein Administration of the invention therefore may be in the form of a paste containing a neutral soft bulk binder or vehicle that forms a paste-like composition when mixed with the remaining components of the invention, with the binder keeping all of the ingredients together in the "paste". A preferred binder is a fat, such as margarine. Alternatively, ingestible melting wax or medicinal clay or other safely ingestible substances known in the art and that form a paste when mixed a set forth herein may be used as the binder. Mixed with the binder are selected non-binder ingredients, preferably spices, condiments and/or seasonings, and salt(s), for placement on selected parts of the tongue, followed by a small quantity of food products smeared with the paste, allowing the patients to eliminate or greatly reduce dependence on food products that they crave. For a liquid craved substance, the powdered non-binder components of the paste are mixed with the liquid for consumption by the person after the initial paste treatments of the tongue. As used herein, the word "non-binder" ingredient includes spices, condiments and/or seasonings, such as mustard and/or other "biting spice" (has a "biting" effect when placed on the tongue; in other words, a sharp, smarting, nipping, keen effect on the tongue), and optionally in the preferred embodiment, a sweetener.

As an added benefit of this type of administration according to the invention, patients who smoke may further be caused to cease or reduce smoking by encouraging the patient to smoke and inhale through the thick coat of paste in the mouth on the tongue. Other components such as sweeteners may optionally be included.

The features of the present invention will be more clearly understood by reference to the following examples, which are not to be construed as limiting the invention.

EXAMPLE 1

Preparation of Composition of the Invention

The method of preparation of the composition of the invention herein is preferably by simply mixing the main components of the preferred embodiment of the invention—a binder such as preferably margarine (or other desired binder), mustard, pepper and salt—to form a simple paste. In addition, a preferred optional ingredient of the compositions disclosed herein is a sweetener, such as saccharin or other sweetener known in the art.

EXAMPLE 2

Example of Compositions of the Invention as a Paste

| Formulation | Margarine (binder) | Mustard | Pepper | Salt |
|---|---|---|---|---|
| T1 | 600 cc (~79%) | 100 cc (~13%) | 40 cc (~5%) | 20 cc (~3%) |
| T2 | 600 cc (~65%) | 200 cc (~22%) | 80 cc (~9%) | 40 cc (~4%) |
| T3 | 240 cc (~48%) | 140 cc (~28%) | 70 cc (~14%) | 50 cc (~10%) |
| T4 | 120 cc (~32%) | 140 cc (~37%) | 70 cc (~18%) | 50 cc (~13%) |
| T5 | 160 cc (~23.5%) | 280 cc (~41%) | 140 cc (~20.5%) | 100 cc (~15%) |

The above composition is prepared as discussed in Example 1. Optionally a sweetener is added, for example, 2 cc of a dried sweetener such as saccharin.

EXAMPLE 3

Use of Composition when Solid Food is the Craved Substance

Persons desiring to decrease their craving for solid foods, for example, chocolate or potato chips, are first provided with the paste on their tongue, as discussed below, and then with the solid food substance mixed with and/or coated with the composition of the invention. Typically, the composition (T1) with the weakest concentration of non-binder constituents is initially administered to a person. If the weakest composition does not have the desired effect of reducing craving for the substance, a stronger concentration is applied at the next treatment, which may be the next month, or the treatments may be more frequent if desired.

Typically, for each treatment, the paste, formulated according to one of the five compositions set forth in Example 2 above, is first applied to the tongue by rubbing on the tongue, preferably on the appropriate location on the tongue as follows: for sweet substances such as chocolate, sodas, cake—on the tip of the tongue; for carbohydrates such as bread, baked potatoes, fries—on the middle of the tongue; and for proteins such as steak, cheese, chicken—on the base of the tongue. The amount used to rub on the tongue is preferably about ⅛ tsp. of the paste. The paste treatment on the tongue is preferably repeated at least a second time (up to a total of about 4 times), followed by drinking water. The tongue treatments and drinking of water are followed by consumption of the desired solid substance that has been coated with the paste composition of the invention or mixed with it as appropriate for the particular substance, so that the paste and substance are simultaneously consumed, and then the person again drinks water. Administration of the paste composition to the tongue creates an aversion to the desired solid substance and decreases or eliminates craving for that food, which effect is increased by subsequent consumption of the solid substance together with the paste composition.

EXAMPLE 4

Use of Composition when a Liquid is the Craved Substance

Persons desiring to reduce their craving for a liquid (for example, sweetened colas or sweetened tea) are provided with the paste on their tongue, formulated according to one of the five compositions set forth in Example 2 above, preferably two administrations as discussed above, followed by drinking water. Then the person drinks a mixture containing the powder components of the composition of the invention (the non-binder components which includes all of the components of one of the compositions set forth in Example 2 except the binder, and optionally, a sweetener), plus the particular liquid substance into which has been mixed non-binder components of the invention (e.g., any of the compositions above in Example 2 without the binder). Preferably, for each ¼ cup of the craved liquid substance, ¼ tbsp. of selected powdered non-binder of the invention is added. Administration of the paste composition to the tongue creates an aversion to the desired liquid substance, which effect is increased by subsequent drinking of the liquid substance together with the non-binder components of the paste composition.

EXAMPLE 5

Use of Composition to Reduce Craving for Tobacco

Persons desiring to reduce their craving for tobacco, for example to cease smoking, are first provided with the paste on the tongue as described above, and then are given a cigarette with the paste coated on the cigarette filter and on the proximal end of the cigarette (the portion to be placed in the mouth), and the patient smokes and inhales through the paste. Administration of the paste composition to the tongue creates an aversion to the desired tobacco product, which effect is increased by subsequent smoking of the tobacco product that has been coated with the paste composition of the invention.

EXAMPLE 6

Treatments with the Invention

Depending on the patient's progress (reduction of craving for previous desired substance), the amount and timing of administration of the composition of the invention is continued monthly (or more often if desired) as needed to reduce the craving for the substance. If a particular patient reports feeling excessive craving for a desired food, additional or stronger paste formulations are administered, while if the patient has reported that the patient's craving has been reduced, the amount and frequency of paste administration are reduced, or eliminated if the person no longer has uncontrollable cravings for the substance.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of reducing a person's craving for a substance, comprising administration to the tongue of the person of a paste composition comprising a binder and seasonings, wherein the administration to the tongue comprises rubbing the paste composition on the person's tongue, wherein the binder comprises margarine and the seasonings comprise mustard, salt and pepper and wherein the paste composition further comprises a sweetener.

2. The method of claim 1, wherein the substance is a solid food product and wherein administration to the tongue is followed by feeding to the person the substance together with the paste composition.

3. The method of claim 2, wherein the substance is coated with the paste composition.

4. The method of claim 1, wherein the substance is a liquid beverage product and wherein administration to the tongue is followed by orally administering to the person a drink comprising of a powder containing mustard, salt and pepper mixed with the liquid beverage product.

5. The method of claim 1, wherein the substance is a sweet substance and the paste composition is administered to the tip of the tongue.

6. The method of claim 1, wherein the substance is a carbohydrate and the paste composition is administered to the middle of the tongue.

7. The method of claim 1, wherein the substance is a protein and the paste is administered to the base of the tongue.

8. The method of claim 1, wherein the substance is a smoked tobacco product, wherein administration to the tongue is followed by providing a tobacco product to the person with the paste composition coating the proximal end of the tobacco product.

* * * * *